United States Patent
Chou et al.

(10) Patent No.: US 11,353,446 B2
(45) Date of Patent: Jun. 7, 2022

(54) METHODS AND DEVICES FOR CORRELATING A BIOMARKER IN A NON-BLOOD BODILY FLUID WITH THE BIOMARKER IN BLOOD

(71) Applicant: Essenlix Corporation, Monmouth Junction, NJ (US)

(72) Inventors: Stephen Y. Chou, Princeton, NJ (US); Wei Ding, Princeton, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 0 days.

(21) Appl. No.: 17/433,092

(22) PCT Filed: Nov. 6, 2020

(86) PCT No.: PCT/US2020/059559
§ 371 (c)(1),
(2) Date: Aug. 23, 2021

(87) PCT Pub. No.: WO2021/092506
PCT Pub. Date: May 14, 2021

(65) Prior Publication Data
US 2022/0091092 A1  Mar. 24, 2022

Related U.S. Application Data

(60) Provisional application No. 62/931,609, filed on Nov. 6, 2019.

(51) Int. Cl.
*G01N 33/487* (2006.01)
*A61B 5/145* (2006.01)
(Continued)

(52) U.S. Cl.
CPC .......... *G01N 33/487* (2013.01); *A61B 5/145* (2013.01); *G01N 33/49* (2013.01); *G01N 33/53* (2013.01);
(Continued)

(58) Field of Classification Search
CPC ...... G01N 33/487; G01N 33/53; G01N 33/66; G01N 35/08; G01N 2001/2276;
(Continued)

(56) References Cited

U.S. PATENT DOCUMENTS 9,383,352 B2    7/2016  Nagalla et al.
2010/0304413 A1  12/2010  Uttenthal et al.
(Continued)

FOREIGN PATENT DOCUMENTS

EP    2724163 A2    4/2014

OTHER PUBLICATIONS

Written Opinion of the International Searching Authority for PCT/US2020/059559 established by the ISA/KR completed on Mar. 3, 2021.
(Continued)

*Primary Examiner* — Dean Kwak

(57) ABSTRACT

Disclosed is a method for correlating a biomarker in a non-blood bodily fluid with the same biomarker in the blood of an individual, including: measuring, in a first period in time, the biomarker in non-blood bodily fluid and measuring the same biomarker in the blood of the same individual to establish an R ratio of [NBBF1]/[BB1], where [NBBF1] is the biomarker concentration in non-blood bodily fluid in the first period in time, and [BB1] is the biomarker concentration in the blood in the first period in time; storing the ratio in a memory; measuring, in a second period in time, the biomarker in non-blood bodily fluid to determine [NBBF2], where [NBBF2] is the biomarker concentration in the non-
(Continued)

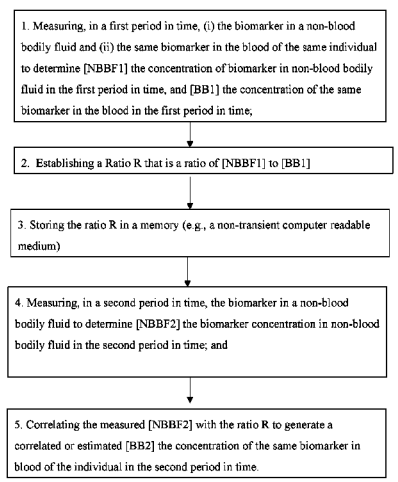

blood bodily fluid in the second period in time; and correlating the measured [NBBF2] with the R ratio to generate a correlated [BB2] biomarker concentration in the blood of the individual in the second period in time. Also disclosed is a device, apparatus, and method for correlating the glucose concentration in a non-blood bodily fluid such as saliva with the glucose in the blood of an individual.

10 Claims, 1 Drawing Sheet

(51) Int. Cl.
    *G01N 33/53*     (2006.01)
    *G01N 33/66*     (2006.01)
    *G01N 33/49*     (2006.01)
    *G01N 33/58*     (2006.01)
    *G01N 35/08*     (2006.01)
    *G01N 1/22*     (2006.01)

(52) U.S. Cl.
    CPC ............. *G01N 33/58* (2013.01); *G01N 33/66* (2013.01); *G01N 35/08* (2013.01); *G01N 2001/2276* (2013.01)

(58) Field of Classification Search
    CPC ... G01N 2021/0118; G01N 2021/0181; G01N 33/49; G01N 33/58; G01N 33/54386; G01N 2201/0662; G01N 2021/0325; G01N 2458/00; A61B 5/145
    See application file for complete search history.

(56) References Cited

U.S. PATENT DOCUMENTS

2017/0181669 A1    6/2017    Lin et al.
2018/0321267 A1*  11/2018  Kennedy ................ G16B 99/00

OTHER PUBLICATIONS

Williamson, S. et al., 'Comparison of Biomarkers in Blood and Saliva in Healthy Adults',Hindawi Publishing Corporation Nursing Research and Practice, vol. 2012, Article ID 246178, internal pp. 1-4, Mar. 1, 2012, pp. 1-3; Table 1.

* cited by examiner

1. Measuring, in a first period in time, (i) the biomarker in a non-blood bodily fluid and (ii) the same biomarker in the blood of the same individual to determine [NBBF1] the concentration of biomarker in non-blood bodily fluid in the first period in time, and [BB1] the concentration of the same biomarker in the blood in the first period in time;

2. Establishing a Ratio R that is a ratio of [NBBF1] to [BB1]

3. Storing the ratio R in a memory (e.g., a non-transient computer readable medium)

4. Measuring, in a second period in time, the biomarker in a non-blood bodily fluid to determine [NBBF2] the biomarker concentration in non-blood bodily fluid in the second period in time; and 5. Correlating the measured [NBBF2] with the ratio R to generate a correlated or estimated [BB2] the concentration of the same biomarker in blood of the individual in the second period in time.

METHODS AND DEVICES FOR CORRELATING A BIOMARKER IN A NON-BLOOD BODILY FLUID WITH THE BIOMARKER IN BLOOD

CROSS REFERENCING

This application is a National Stage entry (§ 371) application of International Application No. PCT/US2020/059559, filed on Nov. 6, 2020, which claims the benefit of U.S. Provisional Patent Application No. 62/931,609, filed on Nov. 6, 2019, which is incorporated herein in its entirety for all purposes.

BACKGROUND

The present application relates to, among other things, methods and devices for correlating a biomarker in a non-blood bodily fluid with the biomarker in blood.

In many situations, measuring a biomarker in non-blood bodily fluid is preferred over that in blood, because (a) it can avoid cutting into skin or inserting a needle into vein, and (b) it is easy, fast, and painless. However, the relationship of a biomarker concentration of in a non-blood fluid to that in blood can vary from a person to a person, making it difficult often impossible to use a single universal conversation relationship/constant for a conversion in all people. For example, the relationship of the glucose concentration in saliva to that in blood varies from person to person, since each person's saliva glands have their own uniqueness. However, for a person, the conversion constant/relationship of a biomarker in a non-bodily fluid to that in blood is often fixed. Therefore, it is possible that by measuring the conversion constant/relationship between a biomarker concentration in a non-bodily fluid to that in blood for each individual and then using the conversion constant/relationship to convert a measurement a biomarker in a non-blood bodily fluid into that in blood for that individual, hence avoiding a further using a blood test. This is one aspect of the present invention.

SUMMARY

A method for correlating a biomarker such as glucose in a non-blood bodily fluid such as saliva with the same biomarker in the blood of an individual.

The disclosed methods in the present invention provide a convenient and painless alternative to conventional blood-letting procedures used in health care and medicine.

In one or more embodiment, the present invention provides:

A method for correlating a biomarker in a non-blood bodily fluid with the same biomarker in the blood of an individual, comprising:

measuring, in a first period in time, (i) the biomarker in a non-blood bodily fluid and (ii) the same biomarker in the blood of the same individual to determine [NBBF1] the concentration of biomarker in non-blood bodily fluid in the first period in time, and [BB1] the concentration of the same biomarker in the blood in the first period in time;

establishing a Ratio R that is a ratio of [NBBF1] to [BB1];

storing the ratio R in a memory (e.g., a non-transient computer readable medium);

measuring, in a second period in time, the biomarker in a non-blood bodily fluid to determine [NBBF2] the biomarker concentration in non-blood bodily fluid in the second period in time; and correlating the measured [NBBF2] with the ratio R to generate a correlated or estimated [BB2] the concentration of the same biomarker in blood of the individual in the second period in time.

An exemplary flowchart of the present invention is given in FIG. 1.

In certain embodiments, the first period further comprising S number of sub-first periods, wherein, for each of the sub-first-periods of S, measuring (i) the biomarker in a non-blood bodily fluid and (ii) the same biomarker in the blood of the same individual to determine [NBBF1-s] the concentration of biomarker in non-blood bodily fluid in the first period in time, and [BB1-s] the concentration of the same biomarker in the blood in the first period in time, and (b) establishing a Ratio R that is a ratio of [NBBF1-s] to [BB1-s], wherein the s is "the s-th" of the sub-first-periods of S;

establishing a Ratio R for the sub-first-period of S, that is a ratio of [NBBF1-S] to [BB1-S];

storing the ratio R's of the sub-first-periods in a memory (e.g., a non-transient computer readable medium);

measuring, in a second period in time, the biomarker in a non-blood bodily fluid to determine [NBBF2] the biomarker concentration in non-blood bodily fluid in the second period in time; and correlating the measured [NBBF2] with the ratio R of the sub-first-periods to generate a correlated or estimated [BB2] the concentration of the same biomarker in blood of the individual in the second period in time.

In certain embodiments, the device for measuring the biomarker in non-blood bodily fluid for the first period and the device for measuring the biomarker in blood are in same location. In certain embodiments, the two devices are in different locations.

In certain embodiments, the device for measuring the biomarker in non-blood bodily fluid for the first period and the device for measuring the biomarker in blood are the same device.

In certain embodiments, the same methods and the devices of the present invention work for non-flowable samples (including samples that are hard to flow on their own).

The terms "Ratio R", "R ratio" and "R" are interchangeable.

BRIEF DESCRIPTION OF THE DRAWINGS

The drawings if any, described below, are for illustration purposes only. In some Figures, the drawings are in scale and not to scale in other Figures. For clarity purposes, some elements are enlarged when illustrated in the Figures. The drawings are not intended to limit the scope of the disclosure.

FIG. 1. An exemplary flowchart of the present invention.

DETAILED DESCRIPTION

The following detailed description illustrates certain embodiments of the invention by way of example and not by way of limitation. If any, the section headings and any subtitles used herein are for organizational purposes only and are not to be construed as limiting the subject matter described in any way. The contents under a section heading and/or subtitle are not limited to the section heading and/or subtitle, but apply to the entire description of the present invention.

In one or more embodiments, the present invention provides, for example:

A method for correlating a biomarker in a non-blood bodily fluid with the same biomarker in the blood of an individual, comprising:

measuring, in a first period in time, (i) the biomarker in non-blood bodily fluid and (ii) the same biomarker in the blood of the same individual to determine [NBBF1] the concentration of biomarker in non-blood bodily fluid in the first period in time, and [BB1] the concentration of the same biomarker in the blood in the first period in time;

establishing a ratio R that is a ratio of [NBBF1] to [BB1];

storing the ratio R in a memory (i.e., non-transient computer readable medium);

measuring, in a second period in time, the biomarker in non-blood bodily fluid to determine [NBBF2] the biomarker concentration in non-blood bodily fluid in the second period in time; and correlating the measured [NBBF2] with the ratio R to generate a correlated or estimated [BB2], the concentration of the same biomarker in the blood of the individual in the second period in time.

A device comprising: a first region for depositing a first sample; and a second region for depositing a second sample, wherein the first and second regions are physically separated and fluidically isolated on the same surface, on the same sample card.

The R ratio for different individuals can be different. For the same individual, the R ratio can change after a period time. One aspect of the present invention is to establish an R ratio for an individual and/or re-calibrate her or his R ratio after a period of time and/or periodically.

The method of any prior embodiment, further comprising periodically calibrating the ratio R to establish a recalibrated [NBBFX]/[BBX] ratio (i.e., R-X), where X is the $n^{th}$ period of time. In some embodiments n is for 3 to 100. In some other embodiments n is greater than 100.

Establishing R Ratio

The relevance of an R ratio can significantly depend upon factors of, for example: (i) the number of paired measurements used to establish R ratio; (ii) the time interval between the blood biomarker test and the non-blood-body-fluid biomarker test in a paired test (since a biomarker concentration in an individual body can change over the time); (iii) the instruments and/or methods used to do the tests (since different instruments and/or methods can give a different reading for the same sample); or (iv) any combination thereof.

The method of any prior embodiment, wherein calibrating is selected from: one pair of calibration tests; or several pairs of calibration tests, e.g., for 2 to 50 pairs, and the calibration tests are over a period of time to establish an [NBBFA]/[BBA] average ratio, where [NBBFA] is the average biomarker concentration in non-blood bodily fluid and [BBA] is the average biomarker concentration in the blood of the individual over the period of time.

In some embodiments the methods can include one or more of the following, for example:

determining an R for each individual;
re-calibrating the R ratio for each individual;
establishing the R ratio at different time of the day;
establishing the R ratio over a year;
other biomarkers (e.g., metabolites, nucleic acids, cell free DNAs RNAs, and like entities);
other body fluids (e.g., sweat, urine, tears, and like entities);

using a Qmax card having both blood glucose and saliva glucose capability to measure the analyte in the different samples simultaneously or at the same, i.e., multiplexing of substantively different samples in the same sample card at the same time. For additional examples of Applicant's multiplexing technology and methodolgy in similar cards or applications, see ESX-103PRV, ESX-106PRV (e.g., p. 13-17), and ESX-029WO (e.g., p. 140-146).

A method of establishing an R ratio, comprising: measuring a pair of BB and NBBF samples within a time interval of, for example, 1 hour or less, 50 min or less, 40 min or less, 30 min or less, 20 min or less, 15 min or less, 10 min or less, 5 min or less, including intermediate values or ranges.

A method of establishing an R ratio, comprising: measuring pairs of BB and NBBF samples, wherein all of the BB samples are measured using the same instrument, and all of the NBBF samples are measured by another or by the same instruments and/or methods.

A method of establishing an R ratio, comprising: measuring pairs of BB and NBBF samples within a time interval of, for example, 1 hour or less, 50 min or less, 40 min or less, 30 min or less, 20 min or less, 15 min or less, 10 min or less, 5 min or less, including intermediate values or ranges, measuring pairs of BB and NBBF samples, wherein all of the BB samples are measured using the same instrument, and all of the NBBF samples are measured by another or by the same instruments and/or methods.

Correlating NBBF with an R Ratio to Generate a Correlated BB

The relevance of correlated BB generated by correlating NBBF with an R ratio can significantly depend upon the instruments and/or methods that used establish R ratio and measure NBBF.

A method of correlating NBBF with an R ratio to generate a correlated BB, comprising: measuring NBBF using the same instrument and/or method used for establishing the R ratio.

Recalibrating the R Ratio

The method of any prior embodiment, wherein periodically calibrating is accomplished in a period selected, for example, from hourly, daily, weekly, monthly, semi-annually, annually, or a combination thereof, including intermediate values and ranges.

The method of any prior embodiment, wherein establishing a recalibrated [NBBFX]/[BBX] ratio is accomplished in at least one period of time selected from: each minute, each hour, each morning, each noon day, each night, each midnight, each day, each week, each month, each semi-annual, each annual, each bi-annual, including intermediate periods-in-time and ranges.

The method of any prior embodiment, wherein correlating is accomplished by solving for [BB2] in the formula:

$$[NBBF2]/[BB2]=R,$$

or when rearranged and substituting for R:

$$[BB2]=[BB1]/[NBBF1][NBBF2].$$

The method of any prior embodiment, wherein the difference between the first time period and the second time period is at least one of: from 5 to 10 minutes, from 20 to 30 minutes, from 30 to 40 minutes, from 40 to 50 minutes, from 50 to 60 minutes, hourly, daily, weekly, monthly, semi-annually, annually, or bi-annually, including intermediate values and ranges.

The method of any prior embodiment, wherein storing the ratio in a memory is accomplished with a mobile communication device.

The method of any prior embodiment, wherein the non-blood bodily fluid is saliva, and the periodically calibrating is accomplished in a period selected from at least one interval of hourly, daily, weekly, monthly, semi-annually, annually, or a combination thereof, including intermediate values and ranges.

The method of any prior embodiment, further comprising applying machine learning (ML) to improve the accuracy of the method by human comparison of, for example, preliminary results, secondary results, or tertiary results, generated by the presently disclosed device (card having segregated sample deposition regions) and associated imaging apparatus.

A method for correlating the glucose concentration in a non-blood bodily fluid with the glucose in the blood of an individual, comprising:

measuring, in a first period in time, the glucose in a non-blood bodily fluid and measuring the glucose in the blood of the same individual to establish a [GNBF1]/[GB1] ratio, where [GNBF1] is the glucose concentration in the non-blood bodily fluid in the first period in time, and [GB1] is the glucose concentration in the blood of the individual in the first period in time;

storing the [GNBF1]/[GB1] ratio in a memory;

measuring [GNBF2] in a second period in time, the glucose concentration in the non-blood bodily fluid; and correlating the measured [GNBF2] with the [GNBF1]/[GB1] ratio to generate a correlated estimated [BB2] glucose concentration in blood of the individual in the second period in time.

The method of any prior embodiment, wherein the non-blood bodily fluid is saliva.

The method of any prior embodiment, further comprising periodically calibrating the [GNBF1]/[GB1] ratio to establish a recalibrated [GNBFX]/[GBX] ratio, where X is the $n^{th}$ period of time where n is for 3 to 100.

The method of any prior embodiment, wherein establishing a recalibrated [NBBFX]/[BBX] ratio is accomplished in at least one period-of-time interval selected from: each minute, each hour, each morning, each noon day, each night, each midnight, each day, each week, each month, each semi-annual, each annual, each bi-annual, including intermediate periods-in-time and ranges.

The method of any prior embodiment, wherein storing the [GNBF1]/[GB1] ratio in a memory is accomplished in a mobile communication device and analyzed by software in the mobile communication device.

Bracketed concentrations such as [NBBF2] is the biomarker concentration in a non-blood bodily fluid and is typically expressed in units of, for example, milligrams per deciliter (mg/dL).

Non-Blood Bodily Fluids

Some examples of the biomarkers for the present invention, comprising: saliva, sweat, urine, tears, or like entities.

In certain embodiments, the same methods and the devices of the present invention work for non-flowable samples (including samples that are hard to flow on their own). One of example is to use QMAX that uses to two plates to deform a non-flowable sample into a thin layer for assaying.

Examples of biological samples that applicable to the present invention include but are not limited to, blood, serum, plasma, a nasal swab, a nasopharyngeal wash, saliva, urine, gastric fluid, spinal fluid, tears, stool, mucus, sweat, earwax, oil, a glandular secretion, cerebral spinal fluid, tissue, semen, vaginal fluid, interstitial fluids derived from tumorous tissue, ocular fluids, spinal fluid, a throat swab, breath, hair, finger nails, skin, biopsy, placental fluid, amniotic fluid, cord blood, lymphatic fluids, cavity fluids, sputum, pus, microbiota, meconium, breast milk, exhaled condensate and/or other excretions. The samples may include nasopharyngeal wash. Nasal swabs, throat swabs, stool samples, hair, finger nail, ear wax, breath, and other solid, semi-solid, or gaseous samples may be processed in an extraction buffer, e.g., for a fixed or variable amount of time, prior to their analysis. The extraction buffer or an aliquot thereof may then be processed similarly to other fluid samples if desired. Examples of tissue samples of the subject may include but are not limited to, connective tissue, muscle tissue, nervous tissue, epithelial tissue, cartilage, cancerous sample, or bone.

In certain embodiments, a non-flowable is dissolved in a solution first before being measured.

Biomarkers

The biomarkers that can be measured using the methods and the devices of the present invention comprising molecules, proteins, nucleic acid (e.g. DNA, RNA), cells, or nanoparticles.

Some examples of the biomarkers for the present invention, include but not limited to:

Lipids Panel Biomarkers:
1) Total Cholesterol—A waxy, fat like substance that travels throughout the body in carrier lipoproteins (HDL, LDL, and VLDL); a precursor to steroid hormones and bile salts.
2) Triglycerides—Measures blood levels of the major storage form of fat in our bodies; also called triacylglycerols.
3) LDL-C—The amount of cholesterol associated with Low Density Lipoprotein (LDL) particles in the blood.
4) HDL-C—The amount of cholesterol associated with High Density Lipoprotein (HDL) particles in the blood.

Comprehensive Metabolic Panel Biomarkers:
(All includes Lipids Panel: Total Cholesterol, Triglycerides, LDL-C, and HDL-C)
1) Glucose—Blood sugar concentration;
2) BUN (Blood Urea Nitrogen)—A marker of kidney function.
3) Creatinine—A byproduct of creatine breakdown.
4) Sodium—A positively charged electrolyte, necessary for muscle contraction, nutrient absorption, neurological functioning, pH balance.
5) Potassium—A positively charged electrolyte, necessary for muscle contraction, pH balance, nerve signal conduction, and action potentials.
6) Chloride—A negatively charged electrolyte; important for maintaining cellular equilibrium across cell membranes and for the production of stomach acid.
7) Carbon dioxide ($CO_2$)—Measures blood bicarbonate and is a surrogate marker for $CO_2$ gas.
8) Uric Acid—End product of DNA purine base metabolism and excretion in the kidneys;
9) Albumin—The most abundant plasma protein in serum, synthesized in the liver, binds to other compounds in the blood and contributes to the plasma osmotic gradient.
10) Globulin—A plasma protein with different subtypes.
11) Calcium—Plays many roles in the body including teeth and bone health, clotting, neurotransmitter function, muscle contraction and enzyme activity.
12) Phosphorus—A mineral involved in DNA and RNA synthesis, part of ATP, helps activate enzymes.
13) Alkaline Phosphatase (ALP)—An enzyme found in the liver, bone, kidneys, small intestine, and placenta.

14) Alanine amino transferase (ALT or SGPT)—An enzyme found in highest concentrations in the liver but also in smaller amounts in heart, muscle and kidney.
15) Aspartate amino transferase (AST or SGOT)—An intracellular enzyme that is usually elevated due to active tissue and cellular destruction.
16) LDH—Lactate dehydrogenase;
17) Total Bilirubin—A byproduct of red blood cell breakdown and an important component of bile; functions as an antioxidant.
18) GGT—An enzyme found primarily in the liver, kidney, and pancreas.
19) Iron—Measures iron bound to transferrin and represents ~1/4 of the total iron binding capacity of transferrin. By itself, is a relatively poor marker of iron status.
20) TIBC—Measures the iron-binding capacity of transferrin.

Additional Common and Recommended Biomarkers:
1) C-Reactive Protein
2) Cortisol
3) DHEA-Sulfate
4) Estimated Glomerular Filtration Rate (eGFR)
5) Estradiol
6) Ferritin: The body's iron binding protein.
7) Folate
8) Hemoglobin A1c
9) Homocysteine
10) Progesterone
11) Prostate Specific Ag (PSA)
12) Testosterone
13) Thyroid-Stimulating Hormone
14) Vitamin D, 25-Hydroxy
15) Brain natriuretic peptide (BNP)

Misc Blood Tests:
1) ABO Grouping (Blood Typing)—Test used for classifying blood types.
2) Antinuclear antibody (ANA)—General test for autoimmune disease
3) Aluminum (Blood)—This blood test measures Aluminum levels.
4) Alcohol
5) Arsenic (Blood)—This blood test is used to measure Arsenic levels.
6) Sexually transmitted diseases (STDs)—No single test exists for all infectious agents. Screening of sexually transmitted infections (STIs) typically includes syphilis, *trichomonas*, gonorrhea, *chlamydia*, herpes, hepatitis and HIV.

Complete Blood Count (CBC) Biomarkers:
RBC: Red blood cell count (corpuscles); Hemoglobin, Hematocrit, MCV: Mean Corpuscular Volume; MCH: Mean Corpuscular Hemoglobin; MCHC: Mean Corpuscular Hemoglobin Concentration; Platelets; MPV; RDW: Red blood cell distribution width; Absolute Neutrophils; Absolute Lymphocytes; Absolute Monocytes; Absolute Eosinophils; Absolute Basophils.

Anemia Biomarkers:
Erythropoietin (EPO), Reticulocytes, Ferritin, Soluble Transferrin Receptor (sTrR), Folic Acid (folates), Transferrin, Hemoglobin, Unsaturated Iron Binding Capacity (UIBC), Iron, Vitamin B12, Iron Saturation.

Autoimmune Disease Biomarkers:
Anti-Double Stranded DNA Ab (dsDNA), Anti-Sjogren Syndrome Ab (SS-B/La), Anti-Nuclear Ab (ANA), Anti-Ribonucleo Protein Ab (RNP), Anti-Smooth Muscle Ab (ASMA), Anti-Mitochondrial Ab (AMA), Anti-Sjogren Syndrome Ab (SS-A/Ro), Anti-Thyroid Peroxidase Ab (TPO).

Bone Diseases Biomarkers:
Alkaline Phosphatase (ALP), Osteocalcin, Aminoterminal Propeptide Type 1 Collagen (PINP), Parathyroid Hormone (PTH), Bone Specific Alkaline Phosphatase (BSAP), Tartrate Resistant Acid Phosphatase-5b (TRACP5b), Calcium (Ca), Vitamin D, 1,25 Dihydroxy, C-Terminal Type I Collagen Telopeptide (CTx), Vitamin D, 25 Hydroxy, N-terminal Type I Collagen Telopeptide (NTx).

Cardiac Markers:
Apolipoprotein E (Apo E), Endothelin-1, Brain Natriuretic Peptide (BNP), LDH, CK, Potassium, CKMB, Pro-B-type Natriuretic Peptide (Pro-BNP), C-Reactive Protein (CRP), Troponin I, CRPhs (ultrasensitive).

Diabetes Biomarkers:
C-Peptide, HbA1c, Cholesteryl Ester Transfer Protein (CETP), IA-2 Antibody, Free Fatty Acids (FFA), Insulin, Fructosamine, Insulin Growth Factor (IGF-1), Glucagon, Microalbumin, Glucose, Proinsulin, Glutamate Decarboxylase-65 (GAD-65) Antibody.

Endocrinology Biomarkers:
Alpha-Foetoprotein, Growth Hormone, Adrenal Corticotrophic Hormone (ACTH), Growth Releasing Factor (GRF), Corticosterone, Prolactin, Cortisol, Testosterone, Follicle Stimulating Hormone (FSH).

Gastroenterology Biomarkers:
Gastrine, Lipase.

Infectious Diseases Biomarkers:
Anti HBs, Hepatitis B Viral Load (quantitative), Anti-HBc, Hepatitis C Genotype, Anti-Hbe, Hepatitis C Viral Load (qualitative), Anti-HCV, Hepatitis C Viral Load (quantitative), Anti-HIV I/II, HIV Viral Load (quantitative), *Chlamydia* Trachomalis, Mononucleosis, Cytomegalovirus (CMV), *Mycobacterium tuberculosis*, HBsAg, Neissera Gonorrhoea.

Inflammation/Immunity Biomarkers:
CD Cell Markers*, Immunoglobulins (IgA, IgG, IgM), Clusterin (Apolipoprotein J), Intra-Cellular Adhesion Molecule-1 (ICAM-1)-2plex, C-Reactive Protein (CRP), IP-10 (IL-12p'70)-2-plex, CRPhs (ultrasensitive), ISG15 gene expression, Endothelin-1, ISG56 gene expression, Fibrinogen, Macrophage Inflammatory Protein (MIP 1), Glucose-6-Phosphate Dehydrogenase (G-6-PDH), Macrophage Inflammatory Protein (MIP 1), HLA-A, Matrix Metalloproteinase-2 (MMP-2), HLA-B, Matrix Metalloproteinase-9 (MMP-9), HLA-C, Monokine Induced by IFN (MIG/CXCL9), IFN-alpha, Neopterin, IFN (IL-2,IL-4-IL-10)-4-plex, OAS1 gene expression, IL-10, OAS2 gene expression, IL-10 (IL-2,IL-4,IFN)-4-plex, OAS3 gene expression, IL-1, Rantes/CCL5, IL-2 (IL-4,IL-10-IFN)-4-plex, Serum Amyloid Protein (SAA), IL-4 (IL-2,IL-10,IFN)-4-plex, Tumor Growth Factor (TGF-1), IL-6, Tumor Necrosis Factor (TNF), IL-8, Vascular Adhesion Molecule-1 (VCAM-1)-2 plex.

Lipid Metabolism Biomarkers:
Apolipoprotein AI (Apo AI), Cholesterol, Apolipoprotein AII (Apo AII), HDL-Cholesterol, Apolipoprotein B-100 (Apo B), LDL-Cholesterol (Direct), Apolipoprotein B48 (Apo B48), Lecithin Cholesterol Acyltransferase (LCAT), Apolipoprotein CII (Apo CII), Paraxonase (PON1), Apolipoprotein CIII (Apo CIII), Phosphatidyl Inositol Glycan F (PIGF), Apolipoprotein E (Apo E), Triglycerides.

Nephrology Biomarkers:
  Alpha-GST, Glomerular Filtration Rate, Beta-2-Microglobulin (serum), Microalbumin, Beta-2-Microglobulin (urine), N-Acetyl-Glucosaminidase (NAG), Collagen Type IV, Pi-GST, Creatinine.

Oncology Biomarkers:
  Bcl-2/IGH, Placenta Growth Factor (P1GF), Carbohydrate Antigen 19-9 (CA19-9), Prostate Specific Antigen (PSA), Carcinogenic Embryonic Antigen (CEA), Vascular Endothelial Growth Factor (VEGF), Fibroblast Growth Factor (FGFb).

Thyroid Markers:
  Anti-Thyroid Peroxidase Ab (TPO), Thyroid Stimulating Hormone (TSH), Anti-Thyroglobulin Ab, Total Thyroxin (T4), Free Thyroxin (FT4), Total Triiodothyronin (T3), Free Triiodothyronin (FT3), TSH Receptor Ab, Thyroglobulin.

Pharmacogenomic Biomarkers in Drug Labeling:
  HLA-B, ESR (Hormone Receptor), ERBB2 (HER2), ERBB2 (HER2), EGFR, ALK, GAA, ERBB2 (HER2), ESR (Hormone Receptor), PIK3CA, NAT2, NAT2, CYP2D6, CYP2D6, CYP2D6, ESR, PGR (Hormone Receptor), UGT1A1, CYP2D6, CYP2D6, CYP2D6, PML-RARA, G6PD, Nonspecific (Congenital Methemoglobinemia), G6PD, CD274 (PD-L1), Gene Signature (T-effector), EGFR, ALK, CYP2D6, PDGFRA, F2 (Prothrombin), F5 (Factor V Leiden), PROC, PROS1, SERPINC1 (Antithrombin III), CYP2C9, CD274 (PD-L1), TPMT, NUDT15, UGT1A1, BRAF, UGT1A1, BCR-ABL1 (Philadelphia chromosome), IFNL3 (IL28B), BCR-ABL1 (Philadelphia chromosome), ALK, TNFRSF8 (CD30), CYP2D6, ALK, CYP2C19, CYP2D6, BCR-ABL1 (Philadelphia chromosome), RET, DPYD, MET, HLA-B, HLA-A, NAGS, CYP2D6, CYP2C19, CYP2D6, G6PD, Nonspecific (Congenital Methemoglobinemia), CYP2C9, ALK, TPP1, EGFR, RAS, CYP2D6, G6PD, Nonspecific (Congenital Methemoglobinemia), G6PD, G6PD, TPMT, CYP2C19, CYP2D6, CYP2C19, CYP2D6, CYP2C19, CYP2D6, BRAF, CYP2D6, HBB, ALK, ROS1, BRAF, G6PD, RAS, IFNL3 (IL28B), EGFR, G6PD, Nonspecific (Congenital Methemoglobinemia), G6PD, CYP2D6, IFNL3 (IL28B), BCR-ABL1 (Philadelphia chromosome), IL2RA (CD25 antigen), Nonspecific (Genetic Susceptibility to Malignant Hyperthermia), CYP2D6, CYP2D6, CYP2D6, CYP2C19, CYP2D6, CYP2C19, MYCN, ESR, PGR (Hormone Receptor), UGT1A1, CYP2D6, CYP2D6, CYP2C19, CYP2C9, CYP2C19, CYP2D6, CD274 (PD-L1), Chromosome 17p, ACHR, AQP4, CYP2B6, SLCO1B1, IFNL3 (IL28B), CFTR, CYP2D6, GALNS, F5 (Factor V Leiden), SERPINC1 (Antithrombin III), Chromosome 7, Chromosome 13, PRF1, RAB27A, SH2D1A, STXBP2, STX11, UNC13D, XIAP (Hemophagocytic Lymphohistiocytosis), IDH2, BRAF, RAS, NECTIN4, ROS1, NTRK, FGFR, CYP2C9, ERBB2 (HER2), ESR, PGR (Hormone Receptor), EGFR, G6PD, CYP2D6, CYP2C19, CYP2C19, PROC, PROS1, SERPINC1 (Antithrombin III), DMD, ERBB2 (HER2), ESR (Hormone Receptor), ESR, PGR (Hormone Receptor), ERBB2 (HER2), CYP2D6, CYP2C9, CYP2C19, CYP2D6, DPYD, DPYD, CYP2D6, CYP2C9, G6PD, CYP2D6, CYP2D6, CYP2C19, HLA-B, ERBB2 (HER2), ESR, PGR (Hormone Receptor), CYP2D6, EGFR, CYP2D6, CD33, FLT3, CPDX, HMBS, PPDX (Acute Hepatic *Porphyria*), G6PD, G6PD, G6PD, DMD, ESR, PGR (Hormone Receptor), Nonspecific (NAT), G6PD, Chromosome 17p, Chromosome 11q, MYD88, CYP2D6, KIT, BCR-ABL1 (Philadelphia chromosome), PDGFRB, FIP1L1-PDGFRA, CYP2D6, UGT1A1, AQP4, TTR, BCR-ABL1 (Philadelphia chromosome), HLA-A, Microsatellite Instability, Mismatch Repair, CD274 (PD-L1), ALK, EGFR, UGT1A1, Chromosome 17p, Chromosome 4p;14q, Chromosome 14q;16q, Nonspecific (Genetic Susceptibility to Malignant Hyperthermia), Nonspecific (NAT), CYB5R, CYB5R, CFTR, CFTR, CFTR, IDH1, ERBB2 (HER2), ESR, PGR (Hormone Receptor), CYP2C19, CYP2C19, ERBB2 (HER2), ESR, PGR (Hormone Receptor), HLA-DQA1, HLA-DRB1, NTRK, IFNL3 (IL28B), Chromosome 5q, Microsatellite Instability, Mismatch Repair, CYP2C9, ESR, PGR (Hormone Receptor), Nonspecific (Congenital Methemoglobinemia), G6PD, G6PD, Nonspecific (Congenital Methemoglobinemia), CYP2D6, ALK, ROS1, HBB, F2 (Prothrombin), F5 (Factor V Leiden), PROC, PROS1, SERPINC1 (Antithrombin III), SSTR, G6PD, CYP2D6, CYP2C9, G6PD, Nonspecific (Congenital Methemoglobinemia), TPMT, NUDT15, G6PD, CYB5R, G6PD, CYP2D6, CYP2D6, FLT3, NPM1, KIT, GLA, CYP2D6, BCHE, CYP2D6, HPRT1, G6PD, CYP2D6, CYP2D6, ERBB2 (HER2), ESR, PGR (Hormone Receptor), BCR-ABL1 (Philadelphia chromosome), UGT1A1, BRCA, Genomic Instability (Homologous Recombination Deficiency), G6PD, BRAF, CD274 (PD-L1), Microsatellite Instability, Mismatch Repair, EGFR, ALK, CYP2D6, SMN2, MS4A1 (CD20 antigen), BRCA, ERBB2 (HER2), ESR, PGR (Hormone Receptor), BRCA, Genomic Instability (Homologous Recombination Deficiency), Homologous Recombination Repair, PPP2R2A, PDGFRA, BCR-ABL1 (Philadelphia chromosome), IFNL3 (IL28B), CYP2C19, CYP2D6, EGFR, CYP2C9, CYP2B6, HLA-B, G6PD, Nonspecific (Congenital Methemoglobinemia), ESR (Hormone Receptor), ERBB2 (HER2), CYP2D6, CYP2D6, EGFR, RAS, CYP2C19, CASR, CYP2D6, TTR, UGT1A1, HLA-B, IFNL3 (IL28B), G6PD, BRAF, CD274 (PD-L1), Microsatellite Instability, Mismatch Repair, EGFR, ALK, Tumor Mutational Burden, FGFR2, CYP2D6, ERBB2 (HER2), ESR, PGR (Hormone Receptor), CYP2C9, CYP2C19, HLA-B, CYP2D6, CYP2C9, CYP2D6, BCR-ABL1 (Philadelphia chromosome), CYP2C19, CYP2C9, CYP3A5, CYP2B6, G6PD, CYB5R, G6PD, Nonspecific (NAT), CYP2D6, CYP2D6, CYP2D6, CYP2D6, G6PD, CYP2D6, CYP2C19, ESR (Hormone Receptor), UGT1A1, EGFR, RAS, G6PD, CYB5R, RAS, ESR, PGR (Hormone Receptor), ERBB2 (HER2), CYP2C9, CYP2D6, MS4A1 (CD20 antigen), F5 (Factor V Leiden), G6PD, Nonspecific (Congenital Methemoglobinemia), SLCO1B1, BRCA, CYP2D6, CYP1A2, BRCA, Loss of Heterozygosity (Homologous Recombination Deficiency), UGT1A1, RET, RYR1, IFNL3 (IL28B), CYP2C9, G6PD, Nonspecific (Congenital Methemoglobinemia), ASS1, CPS1, OTC (Urea Cycle Disorders), IFNL3 (IL28B), IFNL3 (IL28B), IFNL3 (IL28B), G6PD, BCHE, G6PD, G6PD, Nonspecific (NAT), G6PD, Nonspecific (NAT), TTR, G6PD, BRCA, ERBB2 (HER2), ESR, PGR (Hormone Receptor), F5 (Factor V Leiden), F2 (Prothrombin), CYP2D6, CYP2D6, IFNL3 (IL28B), CYP2D6, TPMT, NUDT15, CYP2D6, CYP2C19, ERBB2 (HER2), RAS, G6PD, G6PD, CYP2D6, ESR (Hormone Receptor), CYP2D6, BRAF, G6PD, RAS, ERBB2 (HER2), ESR, PGR (Hormone Receptor), PML-RARA, ACADVL, CPT2, HADHA, HADHB (Long-Chain Fatty Acid Oxidation Disorders), CYP2D6, ERBB2 (HER2), CYP2D6, CYP2D6, IL12A, IL12B, IL23A, CYP2D6, POLG, Nonspecific (Urea Cycle Disorders), BRAF, RAS, Chromosome 17p, Chromosome 11q, TP53, IDH1, IDH2, IGH, NPM1, FLT3, CYP2D6, BCR-ABL1 (Philadelphia chromosome), CYP2C19, CYP2D6, HBB, CYP2C9, VKORC1, PROS1, PROC.

Drug Test Marker:

Alcohol, Amphetamines (except methamphetamine), Methamphetamine, MDMA (Ecstasy), Barbiturates (except phenobarbital), Phenobarbital, Benzodiazepines, Cannabis, Cocaine, Codeine, Cotinine (a breakdown product of nicotine), Morphine, Tricyclic antidepressants (TCA's), LSD, Methadone, Steroids, PCP.

Other examples of embodiments are:

1. A method for correlating a biomarker in a non-blood bodily fluid with the same biomarker in the blood of an individual, comprising:

measuring, in a first period in time, the biomarker in non-blood bodily fluid and measuring the same biomarker in the blood of the same individual to establish an R ratio equal to [NBBF1]/[BB1], where [NBBF1] is the biomarker concentration in the non-blood bodily fluid in the first period in time, and [BB1] is the biomarker concentration in the blood in the first period in time;

storing the R ratio in a memory;

measuring, in a second period in time, the biomarker in non-blood bodily fluid to determine [NBBF2], where [NBBF2] is the biomarker concentration in the non-blood bodily fluid in the second period in time; and correlating the measured [NBBF2] with the R ratio to generate a correlated [BB2] biomarker concentration in blood of the individual in the second period in time.

2. The method of embodiments 1, further comprising periodically calibrating the ratio R to establish a recalibrated [NBBFX]/[BBX] ratio, where X is the $n^{th}$ period of time where n is for 3 to 100.

3. The method of embodiments 2, wherein calibrating is selected from: one pair of calibration tests; or several pairs of calibration tests, and the calibration tests are over a period of time to establish an [NBBFA]/[BBA] average ratio, where [NBBFA] is the average biomarker concentration in non-blood bodily fluid and [BBA] is the average biomarker concentration in the blood of the individual over the period of time.

4. The method of embodiments 2, wherein periodically calibrating is accomplished in a period selected from hourly, daily, weekly, monthly, semi-annually, annually, or a combination thereof, including intermediate values and ranges.

5. The method of embodiments 2, wherein establishing a recalibrated [NBBFX]/[BBX] ratio is accomplished in at least one period of time selected from: each minute, each hour, each morning, each noon day, each night, each midnight, each day, each week, each month, each semi-annual, each annual, each bi-annual, including intermediate periods-in-time and ranges.

6. The method of embodiments 1, wherein correlating is accomplished by solving for [BB2] in the formula:

[NBBF2]/[BB2]=R, or rearranged and substituting for R:

[BB2]=[BB1]/[NBBF1][NBBF2].

7. The method of embodiments 1, wherein the difference between the first time period and the second time period is at least one of: from 5 to 10 minutes, from 20 to 30 minutes, from 30 to 40 minutes, from 40 to 50 minutes, from 50 to 60 minutes, hourly, daily, weekly, monthly, semi-annually, annually, or bi-annually, including intermediate values and ranges.

8. The method of embodiments 1, wherein storing the R ratio in a memory is accomplished with a mobile communication device.

9. The method of embodiments 1, wherein the non-blood bodily fluid is saliva, and the periodically calibrating is accomplished in a period selected from at least one interval of hourly, daily, weekly, monthly, semi-annually, annually, or a combination thereof, including intermediate values and ranges.

10. The method of embodiments 1, further comprising applying machine learning (ML) to improve the accuracy of the method by human comparison of at least one of: preliminary results; secondary results; or tertiary results, generated by a device having segregated sample deposition regions and an associated imaging apparatus or an analyte concentration measuring apparatus.

11. A method for correlating the glucose concentration in a non-blood bodily fluid with glucose in the blood of an individual, comprising:

measuring, in a first period in time, the glucose in non-blood bodily fluid and measuring the glucose the blood of the same individual to establish a [GNBF1]/[GB1] ratio (R), where [GNBF1] is the glucose concentration in non-blood bodily fluid in the first period in time, and [GB1] is the glucose concentration in the blood of the individual in the first period in time;

storing the [GNBF1]/[GB1] ratio in a memory;

measuring, in a second period in time, the glucose concentration in non-blood bodily fluid where [GNBF2] is the glucose concentration in non-blood bodily fluid in the second period in time; and correlating the measured [GNBF2] with the [GNBF1]/[GB1] ratio to generate a correlated estimated [BB2] glucose concentration in blood of the individual in the second period in time.

12. The method of embodiments 11, wherein the non-blood bodily fluid is saliva.

13. The method of embodiments 11, further comprising periodically calibrating the [GNBF1]/[GB1] ratio to establish a recalibrated [GNBFX]/[GBX] ratio, where X is the $n^{th}$ period of time where n is for 3 to 100.

14. The method of embodiments 13, wherein establishing a recalibrated [GNBFX]/[GBX] ratio is accomplished in at least one period-of-time interval selected from: each minute, each hour, each morning, each noon day, each night, each midnight, each day, each week, each month, each semi-annual, each annual, each bi-annual, including intermediate periods-in-time and ranges.

15. The method of embodiments 11, wherein storing the [GNBF1]/[GB1] ratio in a memory is accomplished in a mobile communication device and analyzed by software in the mobile communication device.

16. A device comprising:

a first region for depositing a first sample; and a second region for depositing a second sample, wherein the first and second regions are physically separated and fluidically isolated on the same surface.

17. The device of embodiments 16, wherein the first and second regions are separated by space.

18. The device of embodiments 16, wherein the first and second regions are separated by a visible barrier.

19. The device of embodiments 16, wherein the first sample is saliva, and the second sample is blood.

20. The device of embodiments 16, further comprising at least one of: a third region for depositing a third sample, a fourth region for depositing a fourth sample, a fifth region for depositing a fifth sample, or a sixth region for depositing a sixth sample.

Examples of Devices

Example of the devices used for the present invention include, but not limited to: iMOST, QMAX sample holders, and other devices described in U.S. Pat. No. 10,324,009, by Chou and Ding.

In certain embodiments, the sample form a thin layer, wherein the cell is a mon-layer that does not have significant overlap with each other.

In certain embodiments, the sample holder have scale markers, image markers, monitoring markers, or alike.

In certain embodiments, the sample holder comprises X-plate with spacers/pillars that have a substantially uniform height and a nearly uniform cross-section separated from one another by a consistent, defined distance.

For example X-Plate is 175 um thick PMMA with a pillar array of 30×40 um pillar size, 10 um pillar height and 80 um inter space distance, or iMOST Q-Card comprising X-plate with 175 um thick PMMA with a pillar array of 40 um diameter pillar size, 10 um pillar height and 120 um inter space distance.

In certain embodiments, the sample holder use lateral flow of a sample. The sample load in one location and laterally flow between two plates to another location.

I. Plates

In present invention, generally, the plates of CROF are made of any material that (i) is capable of being used to regulate, together with the spacers, the thickness of a portion or entire volume of the sample, and (ii) has no significant adverse effects to a sample, an assay, or a goal that the plates intend to accomplish. However, in certain embodiments, particular materials (hence their properties) ae used for the plate to achieve certain objectives.

In certain embodiments, the two plates have the same or different parameters for each of the following parameters: plate material, plate thickness, plate shape, plate area, plate flexibility, plate surface property, and plate optical transparency.

(i) Plate Materials. The plates are made a single material, composite materials, multiple materials, multilayer of materials, alloys, or a combination thereof. Each of the materials for the plate is an inorganic material, am organic material, or a mix, wherein examples of the materials are given in paragraphs of Mat-1 and Mat-2.

Mat-1: The inorganic materials for the plates include, not limited to, glass, quartz, oxides, silicon-dioxide, silicon-nitride, hafnium oxide (HfO), aluminum oxide (AIO), semi-conductors: (silicon, GaAs, GaN, etc.), metals (e.g. gold, silver, coper, aluminum, Ti, Ni, etc.), ceramics, or any combinations of thereof.

Mat-2: The organic materials for the spacers include, not limited to, polymers (e.g. plastics) or amorphous organic materials. The polymer materials for the spacers include, not limited to, acrylate polymers, vinyl polymers, olefin polymers, cellulosic polymers, noncellulosic polymers, polyester polymers, Nylon, cyclic olefin copolymer (COC), poly (methyl methacrylate) (PMMA), polycarbonate (PC), cyclic olefin polymer (COP), liquid crystalline polymer (LCP), polyamide (PA), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFA), polydimethylsiloxane (PDMS), rubbers, or any combinations of thereof.

In certain embodiments, the plates are each independently made of at least one of glass, plastic, ceramic, and metal. In certain embodiments, each plate independently includes at least one of glass, plastic, ceramic, and metal.

In certain embodiments, one plate is different from the other plate in lateral area, thickness, shape, materials, or surface treatment. In certain embodiments, one plate is the same as the other plate in lateral area, thickness, shape, materials, or surface treatment.

The materials for the plates are rigid, flexible or any flexibility between the two. The rigid (e.g., stiff) or flexibility is relative to a give pressing forces used in bringing the plates into the closed configuration.

In certain embodiments, a selection of rigid or flexible plate are determined from the requirements of controlling a uniformity of the sample thickness at the closed configuration.

In certain embodiments, at least one of the two plates are transparent (to a light). In certain embodiments at least a part or several parts of one plate or both plates are transparent. In certain embodiments, the plates are non-transparent.

(ii) Plate Thickness. In certain embodiments, the average thicknesses for at least one of the pates are 2 nm or less, 10 nm or less, 100 nm or less, 500 nm or less, 1000 nm or less, 2 um (micron) or less, 5 um or less, 10 um or less, 20 um or less, 50 um or less, 100 um or less, 150 um or less, 200 um or less, 300 um or less, 500 um or less, 800 um or less, 1 mm (millimeter) or less, 2 mm or less, 3 mm or less, or a range between any two of the values.

In certain embodiments, the average thicknesses for at least one of the plates are at most 3 mm (millimeter), at most 5 mm, at most 10 mm, at most 20 mm, at most 50 mm, at most 100 mm, at most 500 mm, or a range between any two of the values.

In certain embodiments, the thickness of a plate is not uniform across the plate. Using a different plate thickness at different location can be used to control the plate bending, folding, sample thickness regulation, and others.

(iii) Plate Shape and Area. Generally, the plates can have any shapes, as long as the shape allows a compress open flow of the sample and the regulation of the sample thickness. However, in certain embodiments, a particular shape can be advantageous. The shape of the plate can be round, elliptical, rectangles, triangles, polygons, ring-shaped, or any superpositions of these shapes.

In certain embodiments, the two plates can have the same size or shape, or different. The area of the plates depend on the application. The area of the plate is at most 1 mm2 (millimeter square), at most 10 mm2, at most 100 mm2, at most 1 cm2 (centimeter square), at most 5 cm2, at most 10 cm2, at most 100 cm2, at most 500 cm2, at most 1000 cm2, at most 5000 cm2, at most 10,000 cm2, or over 10,000 cm2, or any arrange between any of the two values. The shape of the plate can be rectangle, square, round, or others.

In certain embodiments, at least one of the plates is in the form of a belt (or strip) that has a width, thickness, and length. The width is at most 0.1 cm (centimeter), at most 0.5 cm, at most 1 cm, at most 5 cm, at most 10 cm, at most 50 cm, at most 100 cm, at most 500 cm, at most 1000 cm, or a range between any two of the values. The length can be as long it needed. The belt can be rolled into a roll.

(iv) Plate Surface Flatness. In many embodiments, an inner surface of the plates are flat or significantly flat, planar. In certain embodiments, the two inner surfaces are, at the closed configuration, parallel with each other. Flat inner surfaces facilitates a quantification and/or controlling of the sample thickness by simply using the predetermined spacer height at the closed configuration. For non-flat inner surfaces of the plate, one need to know not only the spacer height, but also the exact the topology of the inner surface to quantify and/or control the sample thickness at the closed configuration. To know the surface topology needs additional measurements and/or corrections, which can be complex, time consuming, and costly.

A flatness of the plate surface is relative to the final sample thickness (the final thickness is the thickness at the closed configuration), and is often characterized by the term of "relative surface flatness" is the ratio of the plate surface flatness variation to the final sample thickness.

In certain embodiments, the relative surface is less than 0.01%, 0.1%, less than 0.5%, less than 1%, less than 2%, less than 5%, less than 10%, less than 20%, less than 30%, less than 50%, less than 70%, less than 80%, less than 100%, or a range between any two of these values.

(v) Plate Surface Parallelness. In certain embodiments, the two surfaces of the plate is significantly parallel with each other. In certain embodiments, the two surfaces of the plate is not parallel with each other.

(vi) Plate Flexibility. In certain embodiments, a plate is flexible under the compressing of a CROF process. In certain embodiments, both plates are flexible under the compressing of a CROF process. In certain embodiments, a plate is rigid and another plate is flexible under the compressing of a CROF process. In certain embodiments, both plates are rigid. In certain embodiments, both plate are flexible but have different flexibility.

(vii) Plate Optical Transparency. In certain embodiments, a plate is optical transparent. In certain embodiments, both plates are optical transparent. In certain embodiments, a plate is optical transparent and another plate is opaque. In certain embodiments, both plates are opaque. In certain embodiments, both plate are optical transparent but have different optical transparency. The optical transparency of a plate can refer to a part or the entire area of the plate.

(viii) Surface Wetting Properties. In certain embodiments, a plate has an inner surface that wets (e.g., contact angle is less 90 degree) the sample, the transfer liquid, or both. In certain embodiments, both plates have an inner surface that wets the sample, the transfer liquid, or both; either with the same or different wettability. In certain embodiments, a plate has an inner surface that wets the sample, the transfer liquid, or both; and another plate has an inner surface that does not wet (e.g., the contact angle equal to or larger than 90 degree). The wetting of a plate inner surface can refer to a part or the entire area of the plate.

In certain embodiments, the inner surface of the plate has other nano or microstructures to control a lateral flow of a sample during a CROF. The nano or microstructures include, but not limited to, channels, pumps, and others. Nano and microstructures are also used to control the wetting properties of an inner surface.

II. Spacers (i) Spacers' Function. In present invention, the spacers are configured to have one or any combinations of the following functions and properties: the spacers are configured to (1) control, together with the plates, the thickness of the sample or a relevant volume of the sample (Preferably, the thickness control is precise, or uniform or both, over a relevant area); (2) allow the sample to have a compressed regulated open flow (CROF) on plate surface; (3) not take significant surface area (volume) in a given sample area (volume); (4) reduce or increase the effect of sedimentation of particles or analytes in the sample; (5) change and/or control the wetting propertied of the inner surface of the plates; (6) identify a location of the plate, a scale of size, and/or the information related to a plate, or (7) do any combination of the above.

(ii) Spacer Architectures and Shapes. To achieve desired sample thickness reduction and control, in certain embodiments, the spacers are fixed its respective plate. In general, the spacer can have any shape, as long as the spacers are capable of regulating the sample thickness during a CROF process, but certain shapes are preferred to achieve certain functions, such as better uniformity, less overshoot in pressing, etc.

The spacer(s) is a single spacer or a plurality of spacers. (e.g. an array). Certain embodiments of a plurality of spacers is an array of spacers (e.g. pillars), where the inter-spacer distance is periodic or aperiodic, or is periodic or aperiodic in certain areas of the plates, or has different distances in different areas of the plates.

There are two kinds of the spacers: open-spacers and enclosed-spacers. The open-spacer is the spacer that allows a sample to flow through the spacer (e.g., the sample flows around and pass the spacer. For example, a post as the spacer), and the enclosed spacer is the spacer that stop the sample flow (e.g., the sample cannot flow beyond the spacer. For example, a ring shape spacer and the sample is inside the ring). Both types of spacers use their height to regular the final sample thickness at a closed configuration.

In certain embodiments, the spacers are open-spacers only. In certain embodiments, the spacers are enclosed-spacers only. In certain embodiments, the spacers are a combination of open-spacers and enclosed-spacers.

The term "pillar spacer" means that the spacer has a pillar shape and the pillar shape can refer to an object that has height and a lateral shape that allow a sample to flow around it during a compressed open flow.

In certain embodiments, the lateral shapes of the pillar spacers are the shape selected from the groups of (i) round, elliptical, rectangles, triangles, polygons, ring-shaped, star-shaped, letter-shaped (e.g. L-shaped, C-shaped, the letters from A to Z), number shaped (e.g. the shapes like 0 1, 2, 3, 4, . . . . to 9); (ii) the shapes in group (i) with at least one rounded corners; (iii) the shape from group (i) with zig-zag or rough edges; and (iv) any superposition of (i), (ii) and (iii). For multiple spacers, different spacers can have different lateral shape and size and different distance from the neighboring spacers.

In certain embodiments, the spacers can be and/or can include posts, columns, beads, spheres, and/or other suitable geometries. The lateral shape and dimension (e.g., transverse to the respective plate surface) of the spacers can be anything, except, in certain embodiments, the following restrictions: (i) the spacer geometry will not cause a significant error in measuring the sample thickness and volume; or (ii) the spacer geometry would not prevent the out-flowing of the sample between the plates (e.g., it is not in enclosed form). But in certain embodiments, they require some spacers to be closed spacers to restrict the sample flow.

In certain embodiments, the shapes of the spacers have rounded corners. For example, a rectangle shaped spacer has one, several or all corners rounded (like a circle rather 90 degree angle). A round corner often make a fabrication of the spacer easier, and in some cases less damage to a biological material.

The sidewall of the pillars can be straight, curved, sloped, or different shaped in different section of the sidewall. In certain embodiments, the spacers are pillars of various lateral shapes, sidewalls, and pillar-height to pillar lateral area ratio. In a preferred embodiment, the spacers have shapes of pillars for allowing open flow.

(iii) Spacers' Materials. In the present invention, the spacers are generally made of any material that is capable of being used to regulate, together with the two plates, the thickness of a relevant volume of the sample. In certain embodiments, the materials for the spacers are different from that for the plates. In certain embodiments, the materials for the spaces are at least the same as a part of the materials for at least one plate.

The spacers are made a single material, composite materials, multiple materials, multilayer of materials, alloys, or a combination thereof. Each of the materials for the spacers is an inorganic material, am organic material, or a mix, wherein examples of the materials are given in paragraphs of Mat-1 and Mat-2. In a preferred embodiment, the spacers are made in the same material as a plate used in CROF.

(iv) Spacers' Mechanical Strength and Flexibility. In certain embodiments, the mechanical strength of the spacers are strong enough, so that during the compression and at the closed configuration of the plates, the height of the spacers is the same or significantly same as that when the plates are in an open configuration. In certain embodiments, the differences of the spacers between the open configuration and the closed configuration can be characterized and predetermined.

The material for the spacers is rigid, flexible or any flexibility between the two. The rigid is relative to a give pressing forces used in bringing the plates into the closed configuration: if the space does not deform greater than 1% in its height under the pressing force, the spacer material is regarded as rigid, otherwise a flexible. When a spacer is made of material flexible, the final sample thickness at a closed configuration still can be predetermined from the pressing force and the mechanical property of the spacer.

(v) Spacers Inside Sample. To achieve desired sample thickness reduction and control, particularly to achieve a good sample thickness uniformity, in certain embodiments, the spacers are placed inside the sample, or the relevant volume of the sample. In certain embodiments, there are one or more spacers inside the sample or the relevant volume of the sample, with a proper inter spacer distance. In certain embodiments, at least one of the spacers is inside the sample, at least two of the spacers inside the sample or the relevant volume of the sample, or at least of "n" spacers inside the sample or the relevant volume of the sample, where "n" can be determined by a sample thickness uniformity or a required sample flow property during a CROF.

(vi) Spacer Height. In certain embodiments, all spacers have the same pre-determined height. In certain embodiments, spacers have different pre-determined height. In certain embodiments, spacers can be divided into groups or regions, wherein each group or region has its own spacer height. And in certain embodiments, the predetermined height of the spacers is an average height of the spacers. In certain embodiments, the spacers have approximately the same height. In certain embodiments, a percentage of number of the spacers have the same height.

The height of the spacers is selected by a desired regulated final sample thickness and the residue sample thickness. The spacer height (the predetermined spacer height) and/or sample thickness is 3 nm or less, 10 nm or less, 50 nm or less, 100 nm or less, 200 nm or less, 500 nm or less, 800 nm or less, 1000 nm or less, 1 um or less, 2 um or less, 3 um or less, 5 um or less, 10 um or less, 20 um or less, 30 um or less, 50 um or less, 100 um or less, 150 um or less, 200 um or less, 300 um or less, 500 um or less, 800 um or less, 1 mm or less, 2 mm or less, 4 mm or less, or a range between any two of the values.

The spacer height and/or sample thickness is between 1 nm to 100 nm in one preferred embodiment, 100 nm to 500 nm in another preferred embodiment, 500 nm to 1000 nm in a separate preferred embodiment, 1 um (e.g., 1000 nm) to 2 um in another preferred embodiment, 2 um to 3 um in a separate preferred embodiment, 3 um to 5 um in another preferred embodiment, 5 um to 10 um in a separate preferred embodiment, and 10 um to 50 um in another preferred embodiment, 50 um to 100 um in a separate preferred embodiment.

In certain embodiments, the spacer height and/or sample thickness (i) equal to or slightly larger than the minimum dimension of an analyte, or (ii) equal to or slightly larger than the maximum dimension of an analyte. The "slightly larger" means that it is about 1% to 5% larger and any number between the two values.

In certain embodiments, the spacer height and/or sample thickness is larger than the minimum dimension of an analyte (e.g. an analyte has an anisotropic shape), but less than the maximum dimension of the analyte.

For example, the red blood cell has a disk shape with a minim dimension of 2 um (disk thickness) and a maximum dimension of 11 um (a disk diameter). In an embodiment of the present invention, the spacers is selected to make the inner surface spacing of the plates in a relevant area to be 2 um (equal to the minimum dimension) in one embodiment, 2.2 um in another embodiment, or 3 (50% larger than the minimum dimension) in other embodiment, but less than the maximum dimension of the red blood cell. Such embodiment has certain advantages in blood cell counting. In one embodiment, for red blood cell counting, by making the inner surface spacing at 2 or 3 um and any number between the two values, a undiluted whole blood sample is confined in the spacing, on average, each red blood cell (RBC) does not overlap with others, allowing an accurate counting of the red blood cells visually. (Too many overlaps between the RBC's can cause serious errors in counting).

In the present invention, in certain embodiments, it uses the plates and the spacers to regulate not only a thickness of a sample, but also the orientation and/or surface density of the analytes/entity in the sample when the plates are at the closed configuration. When the plates are at a closed configuration, a thinner thickness of the sample gives a less the analytes/entity per surface area (e.g., less surface concentration).

(vii) Spacer Lateral Dimension. For an open-spacer, the lateral dimensions can be characterized by its lateral dimension (sometime being called width) in the x and y-two orthogonal directions. The lateral dimension of a spacer in each direction is the same or different. In certain embodiments, the lateral dimension for each direction (x or y) is. . . .

In certain embodiments, the ratio of the lateral dimensions of x toy direction is 1, 1.5, 2, 5, 10, 100, 500, 1000, 10,000, or a range between any two of the value. In certain embodiments, a different ratio is used to regulate the sample flow direction; the larger the ratio, the flow is along one direction (larger size direction).

In certain embodiments, the different lateral dimensions of the spacers in x and y direction are used as (a) using the spacers as scale-markers to indicate the orientation of the plates, (b) using the spacers to create more sample flow in a preferred direction, or both.

In a preferred embodiment, the period, width, and height.

In certain embodiments, all spacers have the same shape and dimensions. In certain embodiments, each of the spacers have different lateral dimensions.

For enclosed-spacers, in certain embodiments, the inner lateral shape and size are selected based on the total volume of a sample to be enclosed by the enclosed spacer(s), wherein the volume size has been described in the present disclosure; and in certain embodiments, the outer lateral shape and size are selected based on the needed strength to support the pressure of the liquid against the spacer and the compress pressure that presses the plates.

(viii) Aspect Ratio of Height to the Average Lateral Dimension of Pillar Spacer. In certain embodiments, the aspect ratio of the height to the average lateral dimension of the pillar spacer is 100,000, 10,000, 1,000, 100, 10, 1, 0.1, 0.01, 0.001, 0.0001, 0, 00001, or a range between any two of the values.

(ix) Spacer Height Precisions. The spacer height should be controlled precisely. The relative precision of the spacer (e.g., the ratio of the deviation to the desired spacer height) is 0.001% or less, 0.01% or less, 0.1% or less; 0.5% or less, 1% or less, 2% or less, 5% or less, 8% or less, 10% or less, 15% or less, 20% or less, 30% or less, 40% or less, 50% or less, 60% or less, 70% or less, 80% or less, 90% or less, 99.9% or less, or a range between any of the values.

(x) Inter-Spacer Distance. The spacers can be a single spacer or a plurality of spacers on the plate or in a relevant area of the sample. In certain embodiments, the spacers on the plates are configured and/or arranged in an array form, and the array is a periodic, non-periodic array or periodic in some locations of the plate while non-periodic in other locations.

In certain embodiments, the periodic array of the spacers has a lattice of square, rectangle, triangle, hexagon, polygon, or any combinations of thereof, where a combination means that different locations of a plate has different spacer lattices.

In certain embodiments, the inter-spacer distance of a spacer array is periodic (e.g., uniform inter-spacer distance) in at least one direction of the array. In certain embodiments, the inter-spacer distance is configured to improve the uniformity between the plate spacing at a closed configuration.

The distance between neighboring spacers (e.g., the inter-spacer distance) is 1 um or less, 5 um or less, 10 um or less, 20 um or less, 30 um or less, 40 um or less, 50 um or less, 60 um or less, 70 um or less, 80 um or less, 90 um or less, 100 um or less, 200 um or less, 300 um or less, 400 um or less, or a range between any two of the values.

In certain embodiments, the inter-spacer distance is at 400 or less, 500 or less, 1 mm or less, 2 mm or less, 3 mm or less, 5 mm or less, 7 mm or less, 10 mm or less, or any range between the values. In certain embodiments, the inter-spacer distance is a10 mm or less, 20 mm or less, 30 mm or less, 50 mm or less, 70 mm or less, 100 mm or less, or any range between the values.

The distance between neighboring spacers (e.g., the inter-spacer distance) is selected so that for a given properties of the plates and a sample, at the closed-configuration of the plates, the sample thickness variation between two neighboring spacers is, in certain embodiments, at most 0.5%, 1%, 5%, 10%, 20%, 30%, 50%, 80%, or any range between the values; or in certain embodiments, at most 80%, 100%, 200%, 400%, or a range between any two of the values.

Clearly, for maintaining a given sample thickness variation between two neighboring spacers, when a more flexible plate is used, a closer inter-spacer distance is needed.

Specify the accuracy of the inter spacer distance.

In a preferred embodiment, the spacer is a periodic square array, wherein the spacer is a pillar that has a height of 2 to 4 um, an average lateral dimension of from 5 to 20 um, and inter-spacer spacing of 1 um to 100 um.

In a preferred embodiment, the spacer is a periodic square array, wherein the spacer is a pillar that has a height of 2 to 4 um, an average lateral dimension of from 5 to 20 um, and inter-spacer spacing of 100 um to 250 um.

In a preferred embodiment, the spacer is a periodic square array, wherein the spacer is a pillar that has a height of 4 to 50 um, an average lateral dimension of from 5 to 20 um, and inter-spacer spacing of 1 um to 100 um.

In a preferred embodiment, the spacer is a periodic square array, wherein the spacer is a pillar that has a height of 4 to 50 um, an average lateral dimension of from 5 to 20 um, and inter-spacer spacing of 100 um to 250 um.

The period of spacer array is between 1 nm to 100 nm in one preferred embodiment, 100 nm to 500 nm in another preferred embodiment, 500 nm to 1000 nm in a separate preferred embodiment, 1 um (e.g., 1000 nm) to 2 um in another preferred embodiment, 2 um to 3 um in a separate preferred embodiment, 3 um to 5 um in another preferred embodiment, 5 um to 10 um in a separate preferred embodiment, and 10 um to 50 um in another preferred embodiment, 50 um to 100 um in a separate preferred embodiment, 100 um to 175 um in a separate preferred embodiment, and 175 um to 300 um in a separate preferred embodiment.

(xi) Spacer Density. The spacers are arranged on the respective plates at a surface density of greater than one per um2, greater than one per 10 um2, greater than one per 100 um2, greater than one per 500 um2, greater than one per 1000 um2, greater than one per 5000 um2, greater than one per 0.01 mm2, greater than one per 0.1 mm2, greater than one per 1 mm2, greater than one per 5 mm2, greater than one per 10 mm2, greater than one per 100 mm2, greater than one per 1000 mm2, greater than one per 10000 mm2, or a range between any two of the values.

(3) the spacers are configured to not take significant surface area (volume) in a given sample area (volume);

(xii) Ratio of Spacer Volume to Sample Volume. In many embodiments, the ratio of the spacer volume (e.g., the volume of the spacer) to sample volume (e.g., the volume of the sample), and/or the ratio of the volume of the spacers that are inside of the relevant volume of the sample to the relevant volume of the sample are controlled for achieving certain advantages. The advantages include, but not limited to, the uniformity of the sample thickness control, the uniformity of analytes, the sample flow properties (e.g., flow speed, flow direction, etc.).

In certain embodiments, the ratio of the spacer volume r) to sample volume, and/or the ratio of the volume of the spacers that are inside of the relevant volume of the sample to the relevant volume of the sample is less than 100%, at most 99%, at most 70%, at most 50%, at most 30%, at most 10%, at most 5%, at most 3% at most 1%, at most 0.1%, at most 0.01%, at most 0.001%, or a range between any of the values.

(xiii) Spacers Fixed to Plates. The inter spacer distance and the orientation of the spacers, which play a key role in the present invention, are preferably maintained during the process of bringing the plates from an open configuration to the closed configuration, and/or are preferably predetermined before the process from an open configuration to a closed configuration.

In certain embodiments of the present disclosure, spacers are fixed on one of the plates before bring the plates to the closed configuration. The term "a spacer is fixed with its respective plate" means that the spacer is attached to a plate and the attachment is maintained during a use of the plate. An example of "a spacer is fixed with its respective plate" is that a spacer is monolithically made of one piece of material of the plate, and the position of the spacer relative to the plate surface does not change. An example of "a spacer is not fixed with its respective plate" is that a spacer is glued to a plate by an adhesive, but during a use of the plate, the adhesive cannot hold the spacer at its original location on the plate surface (e.g., the spacer moves away from its original position on the plate surface).

In certain embodiments, at least one of the spacers are fixed to its respective plate. In certain embodiments, at two spacers are fixed to its respective plates. In certain embodiments, a majority of the spacers are fixed with their respective plates. In certain embodiments, all of the spacers are fixed with their respective plates.

In certain embodiments, a spacer is fixed to a plate monolithically.

In certain embodiments, the spacers are fixed to its respective plate by one or any combination of the following methods and/or configurations: attached to, bonded to, fused to, imprinted, and etched.

The term "imprinted" means that a spacer and a plate are fixed monolithically by imprinting (e.g., embossing) a piece of a material to form the spacer on the plate surface. The material can be single layer of a material or multiple layers of the material.

The term "etched" means that a spacer and a plate are fixed monolithically by etching a piece of a material to form the spacer on the plate surface. The material can be single layer of a material or multiple layers of the material.

The term "fused to" means that a spacer and a plate are fixed monolithically by attaching a spacer and a plate together, the original materials for the spacer and the plate fused into each other, and there is clear material boundary between the two materials after the fusion.

The term "bonded to" means that a spacer and a plate are fixed monolithically by binding a spacer and a plate by adhesion.

The term "attached to" means that a spacer and a plate are connected together.

In certain embodiments, the spacers and the plate are made in the same materials. In other embodiment, the spacers and the plate are made from different materials. In other embodiment, the spacer and the plate are formed in one piece. In other embodiment, the spacer has one end fixed to its respective plate, while the end is open for accommodating different configurations of the two plates.

In other embodiment, each of the spacers independently is at least one of attached to, bonded to, fused to, imprinted in, and etched in the respective plate. The term "independently" means that one spacer is fixed with its respective plate by a same or a different method that is selected from the methods of attached to, bonded to, fused to, imprinted in, and etched in the respective plate.

In certain embodiments, at least a distance between two spacers is predetermined ("predetermined inter-spacer distance" means that the distance is known when a user uses the plates).

In certain embodiments of all methods and devices described herein, there are additional spacers besides to the fixed spacers.

(xiv) Specific Sample Thickness. In present invention, it was observed that a larger plate holding force (e.g., the force that holds the two plates together) can be achieved by using a smaller plate spacing (for a given sample area), or a larger sample area (for a given plate-spacing), or both.

In certain embodiments, at least one of the plates is transparent in a region encompassing the relevant area, each plate has an inner surface configured to contact the sample in the closed configuration; the inner surfaces of the plates are substantially parallel with each other, in the closed configuration; the inner surfaces of the plates are substantially planar, except the locations that have the spacers; or any combination of thereof.

The spacers can be fabricated on a plate in a variety of ways, using lithography, etching, embossing (nanoimprint), depositions, lift-off, fusing, or a combination of thereof. In certain embodiments, the spacers are directly embossed or imprinted on the plates. In certain embodiments, the spacers imprinted into a material (e.g. plastics) that is deposited on the plates. In certain embodiments, the spacers are made by directly embossing a surface of a CROF plate. The nanoimprinting can be done by roll to roll technology using a roller imprinter, or roll to a planar nanoimprint. Such process has a great economic advantage and hence lowering the cost.

In certain embodiments, the spacers are deposited on the plates. The deposition can be evaporation, pasting, or a lift-off. In the pasting, the spacer is fabricated first on a carrier, then the spacer is transferred from the carrier to the plate. In the lift-off, a removable material is first deposited on the plate and holes are created in the material; the hole bottom expose the plate surface and then a spacer material is deposited into the hole and afterwards the removable material is removed, leaving only the spacers on the plate surface. In certain embodiments, the spacers deposited on the plate are fused with the plate. In certain embodiments, the spacer and the plates are fabricated in a single process. The single process includes imprinting (e.g., embossing, molding) or synthesis.

In certain embodiments, at least two of the spacers are fixed to the respective plate by different fabrication methods, and optionally wherein the different fabrication methods include at least one of being deposition, bonded, fuse, imprinted, and etched.

In certain embodiments, one or more of the spacers are fixed to the respective plate(s) is by a fabrication method of being bonded, being fused, being imprinted, or being etched, or any combination of thereof.

In certain embodiments, the fabrication methods for forming such monolithic spacers on the plate include a method of being bonded, being fused, being imprinted, or being etched, or any combination of thereof Machine Learning Details of the Network are described in detail in a variety of publications including International Application (IA) No. PCT/US2018/017504 filed Feb. 8, 2018, and PCT/US2018/057877 filed Oct. 26, 2018, each of which are hereby incorporated by reference herein for all purposes.

One aspect of the present invention provides a framework of machine learning and deep learning for analyte detection and localization. A machine learning algorithm is an algorithm that is able to learn from data to detect, segment, and classify the analytes from the image of the sample. A more rigorous definition of machine learning is "A computer program is said to learn from experience E with respect to some class of tasks T and performance measure P, if its performance at tasks in T, as measured by P, improves with experience E." It explores the algorithms that can learn from and make predictions on data—such algorithms overcome the static program instructions by making data driven predictions or decisions, through building a model from sample inputs.

Deep learning is a specific kind of machine learning based on a set of algorithms that attempt to model the high level abstractions in data. In a simple case, there might be two sets of neurons: ones that receive an input signal and ones that send an output signal. When the input layer receives an input, it passes on a modified version of the input to the next layer. In a deep network, there are many layers between the input and output (and the layers are not made of neurons but it can help to think of it that way), allowing the algorithm to use multiple processing layers, composed of multiple linear and non-linear transformations.

One aspect of the present invention is two machine learning based analyte detection and localization approaches. The first approach is a deep learning approach and the second approach is a combination of deep learning and computer vision approaches.

(i) Deep Learning Approach. In the first approach, the disclosed analyte detection and localization workflow consists of two stages, training and prediction. We describe training and prediction stages in the following paragraphs.

(a) Training Stage

In the training stage, training data with annotation is fed into a convolutional neural network. Convolutional neural network is a specialized neural network for processing data that has a grid-like, feed forward and layered network topology. Examples of the data include time-series data, which can be thought of as a 1D grid taking samples at regular time intervals, and image data, which can be thought of as a 2D grid of pixels. Convolutional networks have been successful in practical applications. The name "convolutional neural network" indicates that the network employs a mathematical operation called convolution. Convolution is a specialized kind of linear operation. Convolutional networks are simply neural networks that use convolution in place of general matrix multiplication in at least one of their layers.

The machine learning model receives one or multiple images of samples that contain the analytes taken by the imager over the sample holding QMAX device as training data. Training data are annotated for analytes to be assayed, wherein the annotations indicate whether or not analytes are in the training data and where they locate in the image. Annotation can be done in the form of tight bounding boxes which fully contains the analyte, or center locations of analytes. In the latter case, center locations are further converted into circles covering analytes or a Gaussian kernel in a point map.

When the size of training data is large, training machine learning model presents two challenges: annotation (usually done by human) is time consuming, and the training is computationally expensive. To overcome these challenges, one can partition the training data into patches of small size, then annotate and train on these patches, or a portion of these patches. The term "machine learning" refers to algorithms, systems and apparatus in the field of artificial intelligence that often use statistical techniques and artificial neural network trained from data without being explicitly programmed.

The annotated images are fed to the machine learning (ML) training module, and the model trainer in the machine learning module will train a ML model from the training data (annotated sample images). The input data will be fed to the model trainer in multiple iterations until certain stopping criterion is satisfied. The output of the ML training module is a ML model—a computational model that is built from a training process in the machine learning from the data that gives computer the capability to perform certain tasks (e.g. detect and classify the objects) on its own.

The trained machine learning model is applied during the predication (or inference) stage by the computer. Examples of machine learning models include ResNet, DenseNet, etc. which are also named as "deep learning models" because of the depth of the connected layers in their network structure. In certain embodiments, the Caffe library with fully convolutional network (FCN) was used for model training and predication, and other convolutional neural network architecture and library can also be used, such as TensorFlow.

The training stage generates a model that will be used in the prediction stage. The model can be repeatedly used in the prediction stage for assaying the input. Thus, the computing unit only needs access to the generated model. It does not need access to the training data, nor requiring the training stage to be run again on the computing unit.

(b) Prediction Stage

In the predication/inference stage, a detection component is applied to the input image, and an input image is fed into the predication (inference) module preloaded with a trained model generated from the training stage. The output of the prediction stage can be bounding boxes that contain the detected analytes with their center locations or a point map indicating the location of each analyte, or a heatmap that contains the information of the detected analytes.

When the output of the prediction stage is a list of bounding boxes, the number of analytes in the image of the sample for assaying is characterized by the number of detected bounding boxes. When the output of the prediction stage is a point map, the number of analytes in the image of the sample for assaying is characterized by the integration of the point map. When the output of the prediction is a heatmap, a localization component is used to identify the location, and from which, the number of detected analytes is characterized by the entries of the heatmap.

One embodiment of the localization algorithm is to sort the heatmap values into a one-dimensional ordered list, from the highest value to the lowest value. Then pick the pixel with the highest value, remove the pixel from the list, along with its neighbors. Iterate the process to pick the pixel with the highest value in the list, until all pixels are removed from the list.

In the detection component using heatmap, an input image, along with the model generated from the training stage, is fed into a convolutional neural network, and the output of the detection stage is a pixel-level prediction, in the form of a heatmap. The heatmap can have the same size as the input image, or it can be a scaled down version of the input image, and it is the input to the localization component. We disclose an algorithm to localize the analyte center. The main idea is to iteratively detect local peaks from the heatmap. After the peak is localized, we calculate the local area surrounding the peak but with smaller value. We remove this region from the heatmap and find the next peak from the remaining pixels. The process is repeated until all pixels are removed from the heatmap.

In certain embodiments, the present invention provides the localization algorithm to sort the heatmap values into a one-dimensional ordered list, from the highest value to the lowest value. Then pick the pixel with the highest value, remove the pixel from the list, along with its neighbors. Iterate the process to pick the pixel with the highest value in the list, until all pixels are removed from the list.

Algorithm Global Search (heatmap)
Input:
heatmap
Output:
loci
loci 4←{ }
sort(heatmap)
while (heatmap is not empty) {
s←pop(heatmap)
D←{disk center as s with radius R}
heatmap=heatmap \D//remove D from the heatmap add s to loci
}

After sorting, heatmap is a one-dimensional ordered list, where the heatmap value is ordered from the highest to the lowest. Each heatmap value is associated with its corresponding pixel coordinates. The first item in the heatmap is the one with the highest value, which is the output of the pop(heatmap) function. One disk is created, where the center is the pixel coordinate of the one with highest heatmap value. Then all heatmap values whose pixel coordinates resides inside the disk is removed from the heatmap. The algorithm repeatedly pops up the highest value in the current heatmap, removes the disk around it, until all items are removed from the heatmap.

In the ordered list heatmap, each item has the knowledge of the proceeding item, and the following item. When removing an item from the ordered list, we make the following changes:

Assume the removing item is xr, its proceeding item is xp, and its following item is xf.

For the proceeding item xp, re-define its following item to the following item of the removing item. Thus, the following item of xp is now xf.

For the removing item xr, un-define its proceeding item and following item, which removes it from the ordered list.

For the following item xf, re-define its proceeding item to the proceeding item of the removed item. Thus, the proceeding item of xf is now xp.

After all items are removed from the ordered list, the localization algorithm is complete. The number of elements in the set loci will be the count of analytes, and location information is the pixel coordinate for each s in the set loci.

Another embodiment searches local peak, which is not necessary the one with the highest heatmap value. To detect each local peak, we start from a random starting point, and search for the local maximal value. After we find the local peak, we calculate the local area surrounding the peak but with smaller value. We remove this region from the heatmap and find the next peak from the remaining pixels. The process is repeated only all pixels are removed from the heatmap.

Algorithm Local Search (s, heatmap)
Input:
s: starting location (x, y)
heatmap
Output:
s: location of local peak.
We only consider pixels of value>0.
Algorithm Cover (s, heatmap)
Input:
s: location of local peak.
heatmap:
Output:
cover: a set of pixels covered by peak:

This is a breadth-first-search algorithm starting from s, with one altered condition of visiting points: a neighbor p of the current location q is only added to cover if heatmap[p]>0 and heatmap[p]<=heatmap[q]. Therefore, each pixel in cover has a non-descending path leading to the local peak s.

(ii) Mixture of Deep Learning and Computer Vision Approach. In the second approach, the detection and localization are realized by computer vision algorithms, and the classification is realized by deep learning algorithms, wherein the computer vision algorithms detect and locate possible candidates of analytes, and the deep learning algorithm classifies each possible candidate as a true analyte and false analyte. The location of all true analyte (along with the total count of true analytes) will be recorded as the output.

(a) Detection. The computer vision algorithm detects possible candidate based on the characteristics of analytes, including but not limited to intensity, color, size, shape, distribution, etc. A pre-processing scheme can improve the detection. Pre-processing schemes include contrast enhancement, histogram adjustment, color enhancement, de-nosing, smoothing, de-focus, etc. After pre-processing, the input image is sent to a detector. The detector tells the existing of possible candidate of analyte and gives an estimate of its location. The detection can be based on the analyte structure (such as edge detection, line detection, circle detection, etc.), the connectivity (such as blob detection, connect components, contour detection, etc.), intensity, color, shape using schemes such as adaptive thresholding, etc.

(b) Localization. After detection, the computer vision algorithm locates each possible candidate of analytes by providing its boundary or a tight bounding box containing it. This can be achieved through object segmentation algorithms, such as adaptive thresholding, background subtraction, floodfill, mean shift, watershed, etc. Very often, the localization can be combined with detection to produce the detection results along with the location of each possible candidates of analytes.

(c) Classification. The deep learning algorithms, such as convolutional neural networks, achieve start-of-the-art visual classification. We employ deep learning algorithms for classification on each possible candidate of analytes. Various convolutional neural network can be utilized for analyte classification, such as VGGNet, ResNet, MobileNet, DenseNet, etc.

Given each possible candidate of analyte, the deep learning algorithm computes through layers of neurons via convolution filters and non-linear filters to extract high-level features that differentiate analyte against non-analytes. A layer of fully convolutional network will combine high-level features into classification results, which tells whether it is a true analyte or not, or the probability of being a analyte.

Moreover, for people skilled in the field, these two approaches can be further extended and mixed. A mixture of deep learning and computer vision can become even more deep learning oriented by applying computer vision algorithms only for pre-processing of the image, whereas each step in detection, localization, and classification is based on the dedicated deep learning model or using one deep learning model, such as RetinaNet, for doing one step detection and classification.

What is claimed is:

1. A method for correlating a biomarker in a non-blood bodily fluid with the same biomarker in the blood of an individual, comprising:

measuring, in a first period in time, the biomarker in the non-blood bodily fluid and measuring the same biomarker in the blood of the same individual to establish an R ratio equal to [NBBF1]/[BB1], where [NBBF1] is the biomarker concentration in the non-blood bodily fluid in the first period in time, and [BB1] is the biomarker concentration in the blood in the first period in time;

storing the R ratio in a memory;

measuring, in a second period in time, the biomarker in the non-blood bodily fluid to determine [NBBF2], where [NBBF2] is the biomarker concentration in the non-blood bodily fluid in the second period in time; and correlating the measured [NBBF2] with the R ratio to generate a correlated [BB2] biomarker concentration in the blood of the individual in the second period in time.

2. The method of claim 1, further comprising periodically calibrating the ratio R to establish a recalibrated [NBBFX]/[BBX] ratio, where X is the $n^{th}$ period of time where n is for 3 to 100.

3. The method of claim 2, wherein calibrating is selected from: one pair of calibration tests; or several pairs of calibration tests, and the calibration tests are over a period of time to establish an [NBBFA]/[BBA] average ratio, where [NBBFA] is the average biomarker concentration in the non-blood bodily fluid and [BBA] is the average biomarker concentration in the blood of the individual over the period of time.

4. The method of claim 2, wherein periodically calibrating is accomplished in a period selected from hourly, daily, weekly, monthly, semi-annually, annually, or a combination thereof, including intermediate values and ranges.

5. The method of claim 2, wherein establishing a recalibrated [NBBFX]/[BBX] ratio is accomplished in at least one period of time selected from: each minute, each hour, each morning, each noon day, each night, each midnight, each day, each week, each month, each semi-annual, each annual, each bi-annual, including intermediate periods-in-time and ranges.

6. The method of claim 1, wherein correlating is accomplished by solving for [BB2] in the formula:

[NBBF2]/[BB2]=R, or rearranged and substituting for R:

[BB2]=[BB1]/[NBBF1][NBBF2].

7. The method of claim 1, wherein the difference between the first time period and the second time period is at least one of: from 5 to 10 minutes, from 20 to 30 minutes, from 30 to 40 minutes, from 40 to 50 minutes, from 50 to 60 minutes, hourly, daily, weekly, monthly, semi-annually, annually, or bi-annually, including intermediate values and ranges.

8. The method of claim 1, wherein storing the R ratio in a memory is accomplished with a mobile communication device.

9. The method of claim 1, wherein the non-blood bodily fluid is saliva, and the periodically calibrating is accomplished in a period selected from at least one interval of hourly, daily, weekly, monthly, semi-annually, annually, or a combination thereof, including intermediate values and ranges.

10. The method of claim 1, further comprising applying machine learning (ML) to improve the accuracy of the method by human comparison of at least one of: preliminary results; secondary results; or tertiary results, generated by a device having segregated sample deposition regions and an associated imaging apparatus or an analyte concentration measuring apparatus.

* * * * *